(12) United States Patent
Estrada-Parra et al.

(10) Patent No.: US 9,328,152 B2
(45) Date of Patent: May 3, 2016

(54) METHOD FOR OBTAINING A DIALYZABLE LEUKOCYTE EXTRACT

(71) Applicant: INSTITUTO POLITECNICO NACIONAL, México, D.F. (MX)

(72) Inventors: Sergio Estrada-Parra, México, D.F. (MX); Iris Citlati Elvira Estrada-García, México, D.F. (MX); Sonia Mayra Pérez-Tapia, México, D.F. (MX)

(73) Assignee: INSTITUTO POLITECNICO NACIONAL, Mexico City (MX)

( * ) Notice: Subject to any disclaimer, the term of this patent is extended or adjusted under 35 U.S.C. 154(b) by 0 days.

(21) Appl. No.: 14/365,849

(22) PCT Filed: Dec. 17, 2012

(86) PCT No.: PCT/MX2012/000129
§ 371 (c)(1),
(2) Date: Jun. 16, 2014

(87) PCT Pub. No.: WO2013/089550
PCT Pub. Date: Jun. 20, 2013

(65) Prior Publication Data
US 2014/0357840 A1 Dec. 4, 2014

(30) Foreign Application Priority Data
Dec. 16, 2011 (MX) .................. MX/A/2011/013852

(51) Int. Cl.
*C07K 14/52* (2006.01)
*G01N 33/68* (2006.01)
*C07K 14/47* (2006.01)
*G01N 33/50* (2006.01)

(52) U.S. Cl.
CPC ............ *C07K 14/4705* (2013.01); *C07K 14/52* (2013.01); *G01N 33/5011* (2013.01); *G01N 33/68* (2013.01)

(58) Field of Classification Search
None
See application file for complete search history.

(56) References Cited

U.S. PATENT DOCUMENTS

| 4,816,563 | A | 3/1989 | Wilson et al. |
|---|---|---|---|
| 5,080,895 | A | 1/1992 | Tokoro |
| 5,840,700 | A | 11/1998 | Kirkpatrick et al. |
| 5,883,224 | A | 3/1999 | Kirkpatrick et al. |
| 6,468,534 | B1 | 10/2002 | Hennen et al. |
| 2002/0044942 | A1* | 4/2002 | Dopson ...................... 424/184.1 |
| 2003/0031686 | A1 | 2/2003 | Hennen et al. |
| 2008/0081076 | A1* | 4/2008 | Lisonbee et al. .............. 424/535 |

FOREIGN PATENT DOCUMENTS

| DE | 3244607 A1 | 6/1984 |
|---|---|---|
| EP | 0143445 A2 | 6/1985 |
| WO | 9200093 A1 | 1/1992 |
| WO | WO 9200093 * | 1/1992 |
| WO | 9712915 A1 | 4/1997 |
| WO | WO 9712915 * | 4/1997 |
| WO | 2007143957 A2 | 12/2007 |
| WO | WO 2007143957 * | 12/2007 |

OTHER PUBLICATIONS

NLA2004000058 Patent application.

* cited by examiner

*Primary Examiner* — Karlheinz R Skowronek
*Assistant Examiner* — Roy Teller
(74) *Attorney, Agent, or Firm* — Browdy and Neimark, PLLC

(57) ABSTRACT

The present invention relates to a method for producing a transfer factor. The method comprises the following steps: freezing and thawing of peripheral-blood leukocytes, dialysis, tangential ultrafiltration, identification and quantification using high-resolution, molecular-exclusion liquid chromatography, and in vitro biological validation. The resulting product is suitable for medical use.

5 Claims, 3 Drawing Sheets

METHOD FOR OBTAINING A DIALYZABLE LEUKOCYTE EXTRACT

FIELD OF THE INVENTION

The present invention relates to the technical field of production processes for medicinal preparations containing peptides; more particularly, it belongs to the technical field of production processes for medicinal preparations containing leukocitary dialyzable extract.

BACKGROUND OF THE INVENTION

Transfer factors, which are produced by leukocytes and lymphocytes, are small water-soluble polypeptides of about 44 amino acids that stimulate or transfer cell-mediated immunity from one subject to another and through species, but it does not provoke an allergic response. Since the transfer factors are smaller than antibodies, they do not transfer antibody-mediated responses, they are non-immunogenic so they do not induce the production of antibodies. Properties and characteristics of transfer factors have been discussed in U.S. Pat. Nos. 4,816,563, 5,080,895, 5,840,700, 5,883,224, and 6,468,534 patents.

Transfer factors have been described as effective therapeutics for treating herpex simplex virus infection, to treat acne, and for the treatment of infections caused by *Candida albicans*. Also, they have been used to treat cryptosporidiosis in recipients treated with a specific transfer factor. On the other hand, they have also been used for the treatment of small pox, as a pretreatment of children having transfer factor from subjects who had small pox.

For many years diverse methodologies have been used to obtain the transfer factor. For example, patent application WO2007143957 describes a process for obtaining the factor from leukocytes; this process includes the following steps: adjusting the leukocyte homogenate, dialysis and/or ultrafiltration, concentration by lyophilization, adjusting the raw medical solution, interoperative testing, homogenization, prefiltration, ultrafiltration, sterilization by filtration, thermal inactivation, product packaging, and lyophilization. However, in said process a highly raw factor is obtained, since it contains a large number of components that may mask the factor action.

In turn, NLA2004000058 patent describes a method wherein a leucocitary extract is subjected to sterilization by filtration, and chromatography using Sephadex G-15. This process uses as a quality control the chemotaxis test in rat peripheral blood or thymus and spleen lymphocytes. However, as said method is subjected only to a separation by sephadex, it does not guarantee the purity of the factor since it contains multiple components that can interfere with the metabolic action of the factor.

On the other hand, patent application No. US20030031686A1 describes a method for obtaining a transfer factor from chicken eggs. This method consists in immunizing the birds with a particular antigen and from the egg white to obtain a water soluble fraction; this fraction was subjected to three consecutive filtration processes: a) by filter paper, (b) by vacuum using glass-fiber filter, and c) by filtration using a DURAPORE hydrophilic membrane to remove lipids and lipoproteins. The protein-containing fraction is collected, frozen, and lyophilized. Although, this process is extremely simple, it has the drawback of lacking of a low molecular weight polypeptide separation, and therefore the product obtained contains proteins interfering with the transfer factor action.

Another process to obtain transfer factor is that described in the US20020044942 patent application. Said process consists in obtaining the factor from immunized-chicken eggs, and comprises various steps, including filtration, centrifugation, filtration, dialysis, high-performance liquid chromatography, and lyophilization. However, the disadvantage of this process is the difficult handling of eggs when manually separating the yolk and the white, resulting in the protein fraction becoming contaminated with the lipid fraction.

Likewise, U.S. Pat. No. 5,840,700 patent describes a method to obtain a substantially pure transfer facto with a specific activity of at least 5000 units per AU214. The process consists mainly in contacting a sample containing the transfer factor with an immobilized antigen to which the factor binds specifically under conditions favoring the formation of the antigen-transfer factor complex. This complex is subsequently separated by reverse phase, high-resolution liquid chromatography, and high-resolution liquid chromatography by gel filtration. Despite the high degree of purity due to the antigen-specific immobilization step, this process has the great disadvantage of requiring a large amount of antigen, resulting in a fairly expensive process.

Finally, EP0143445A2 patent application describes a method for obtaining a transfer factor from lactating-cows' colustrum. This method basically consists of the following steps: centrifugation to obtain a cell precipitation, removal of casein, ultrafiltration, and dialysis, chromatography, and lyophilization. This process has the great disadvantage of the low availability of caws' or other mammals' colostrum in lactation stage.

SUMMARY OF THE INVENTION

According to the result of the analysis of the state of the art, it can be seen that there is a technical problem with respect to the methodology for obtaining the transfer factor. Said problem consists in lacking of a high-purity transfer factor. This may be a problem emerging from the factor source, for example, from the white of the immunized-hens, or by lacking of specific better purification steps.

In this sense, the present invention reasonably improves the technical problems. In the first instance, obtaining the transfer factor from peripheral-blood allows to avoid the difficult handling of the immunized-hens' eggs stated US20020044942 and US20030031686A1 patent applications. In the same way, there is a major source of factor unlike the cows' colostrum stated in the EP0143445A2 patent application. On the other hand, it has the advantage of obtaining a higher-purity factor when using a purification step based on a ultra-resolution, molecular-exclusion liquid chromatography; this stage primary overcomes the disadvantages present in those processes described in the WO2007143957 and NLa2004000058 patent applications. Finally, this process turns out to be low-cost sin no-antigen is used for the factor purification, unlike that described in U.S. Pat. No. 5,840,700 patent.

In addition, the present invention has a biological validation step of the factor, thereby allowing to reject those transfer factor batches which do not meet said test.

DETAILED DESCRIPTION OF THE INVENTION

Figure 1:
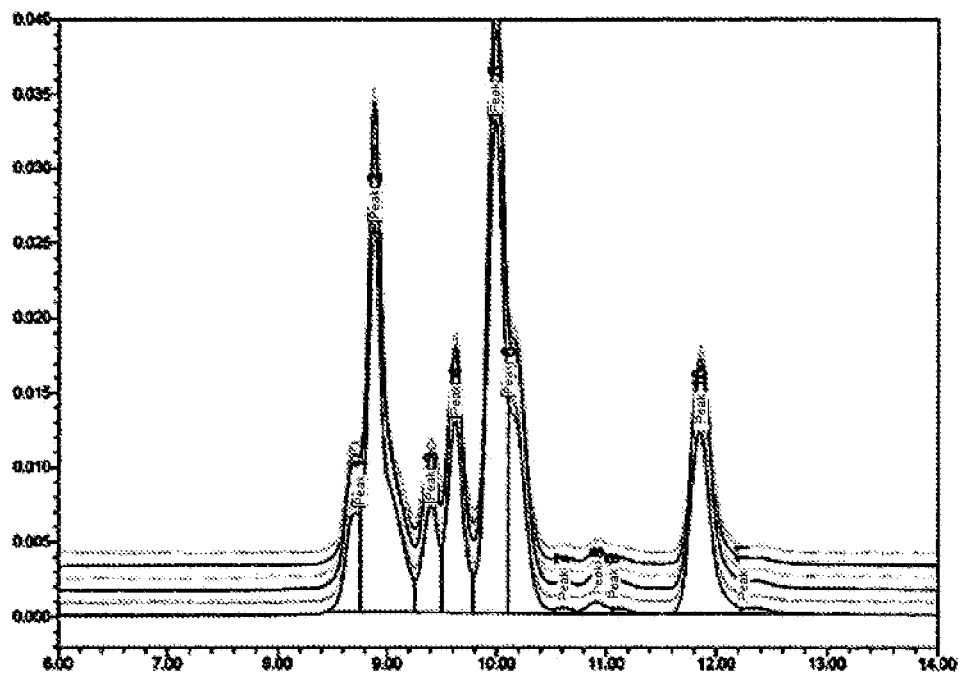
FIG. 1 is a calibration curve of the transfer factor by ultra resolution, molecular-exclusion liquid chromatography. The various lines are various batches to which the testing was applied.

Now, the invention will be described based on particular examples. These examples are illustrative only and do not intend to limit in any way the scope of the invention.

EXAMPLE 1

Freezing/thawing Step

The transfer factor is obtained from leukocyte-concentrate units. The units are frozen and subsequently they are subjected to five freezing/thawing steps. In this sense, the leukocyte-concentrate packages are grouped together to form batches of 20 leukocyte-concentrates in plastic bags. The freezing cycles start storing the batches at −20° C. for one week. After the week, thawing of the leucocyte-concentrate packages is made by locating them in a sink under tap water. When completely thawed, they are got back at −20° C. and stored for a week. And so on, until finishing the five freezing/thawing cycles.

EXAMPLE 2

Dialysis Step

The dialysis process starts cutting off a membrane for 12 KDa to 1.40 meter length. This membrane is placed in a 4 liters beaker containing 2.5 liters Elix water and allow to boil for 10 minutes. After, the dialysis membrane is taken out and it is placed in another 4 liters beaker containing 2.5 liters Elix water and let to boil for 10 minutes. Subsequently the dialysis membrane is taken out and it is placed in another 4 liters beaker containing 2.5 liters Elix water and sterilize for 15 minutes at 121° C. The dialysis membrane remains in the sterile water until use.

Once the dialysis membrane is prepared, said membrane is filled with the leukocitary extract subjected to the freezing/thawing processes. This process begins cleaning the bags containing the leukocitary concentrate with 70% alcohol; later, one of the bag ends is cut using sterile surgical scissors. It is emptied and the leukocitary concentrate contents is measured by decantation into a test tube. Then the test tube contents is poured in a 1 liter glass vial. The steps are repeated with the various bags up to a volume of 1.100 liters of leukocitary concentrate within the vial. Subsequently, 800 milliliters of pisa water is measured in a test tube, and this volume is poured into a 2 liters sterile vial. Using sterile gloves one end of the dialysis membrane is taken out and a knot is made at 10 cm from the end, a second knot is made to 7 cm from the end, and between both ends a surgical thread is attached. After, the other end of the dialysis membrane is taken out and a finger is inserted into the membrane, pushing the dialysis membrane to form an accordion. The finger is removed and the vial's neck is placed instead, taking care to not breaking the membrane. The membrane is taken out and the end having both knots is placed into a 2 liters sterile vial, leaving the surgical thread out of the vial. Then, the end of the surgical thread located out of the vial is taken with surgical pliers, and the entire leukocitary concentrate is poured from the vial by decantation into the funnel, carefully introducing slowly the membrane into the 2 liters vial. Subsequently, the funnel is withdrawn from the end of the dialysis membrane and a double knot is made leaving 3 cm distance. A sterile clamp is placed (clip) between both knots and a sterile aluminum cap is placed and leave dialyzing for 20 hours. Once finished the 20 hours of dialysis, samples are taken for the corresponding analysis. Then, the dialysis product is poured into a 4 liters sterile glass by decantation, trying that the decanted liquid to touch as less as possible the dialysis membrane ends. It is filtered by 0.22 um, it is collected in a 2 liters sterile vial, the volume obtained is measured as a dialysis product, and it is stored at −20° C. until the tangential ultrafiltration begins.

EXAMPLE 3

Tangential Ultrafiltration Step

To perform the product ultrafiltration according to the following: the 10 KDa cartridge is sampled and it will determine the present amount of endotoxin. The system pressures are checked (10 psi at the feed port and 5 psi at the retained). Subsequently, a hose is connected to the feed port in order to install it at the peristaltic pump head and inserting the other end in the carboy containing the dialysated product to 12 KDa. Connect a second hose to the port of the permeated to the filtration unit and insert it into a clean 20 L carboy 20 L labeled as PERMEATED 1. Connect a third hose to the port of retained and insert it in a third 20 L carboy labeled as RETAINED 1 (note: Prepare an additional carboy labeled as RETAINED 1,1 since two carboys of retained product will be obtained). Turn on the peristaltic pump and set it at 1 L/min. Ultrafiltrate the entire product. Measure with a 2 L test tube the total amount of each obtained product. Recycle the RETAINED 1 and RETAINED 1,1 product to zero volume as follows: entering the feed hose into one of the carboys containing the retained product (RETAINED 1 or RETAINED 1.1), entering the hose for retained in the same carboy than the feed hose (RETAINED 1 or RETAINED 1, 1), entering the hose for permeated into another carboy labeling it as PERMEATED 2 (note: as 2 carboys of permeated product will be obtained, another carboy is to be prepared labeling it as PERMEATED 2,1. Turn on the peristaltic pump and set it at 1 L/min. Ultrafiltrate the retained product up to a zero volume. Measure with the 2 L test tube the total volume of the obtained products. The product from the three carboys is homogenized with permeated product (PERMEATED 1, PERMEATED 2 and PERMEATED 2,1) as follows: entering a hose into the carboy containing the product PERMEATED 2,1 installing the hose in the peristaltic pump head and entering the other end in the carboy containing the product PERMEATED 1, scheduling the pump to 1 L/min and moving half of the amount contained in the carboy PERMEATED 2,1 to the PERMEATED 1. Repeat steps a and b to move the other half of the amount of the product PERMEATED 2,1 to the carboy containing the PERMEATED 2, remaining two carboys with permeated product. Two hoses are entered in the carboy PERMEATED 1, they are installed in the two peristaltic pump heads (one pump for each hose) and entering the other ends in the carboy PERMEATED 2. Schedule the peristaltic pumps in opposite directions (on with left turn and the other with right turn) and at a rate of 13 L/min. Start both pumps and hold for 20 min. Identify both carboys as TOTAL PERMEATED. Measure with 2 L test tube the total volume obtained and quantify the proteins. According to the above, carry out an ultrafiltration using a 1 kDa cartridge.

EXAMPLE 4

Figure 2:
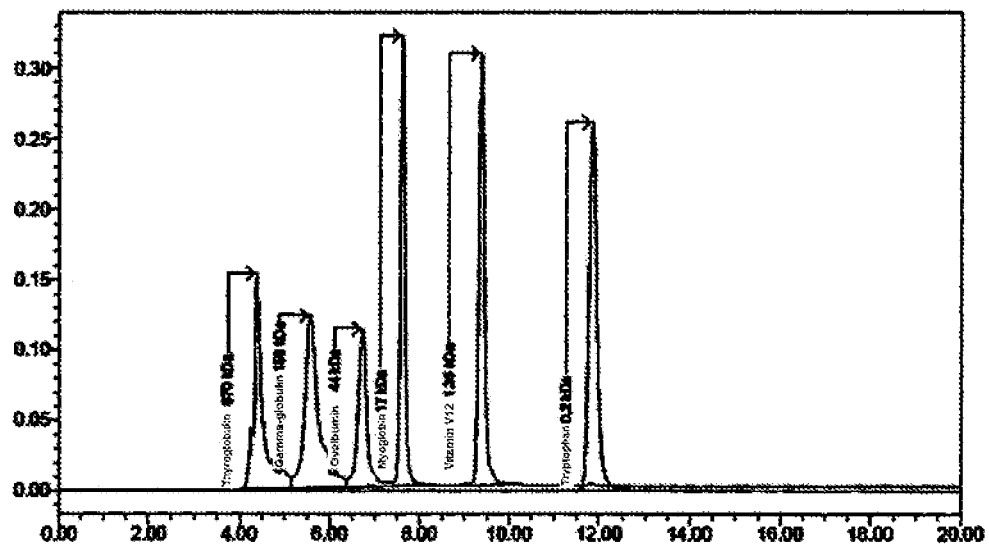
FIG. 2 is a standard curve of molecular weight.
Figure 3:
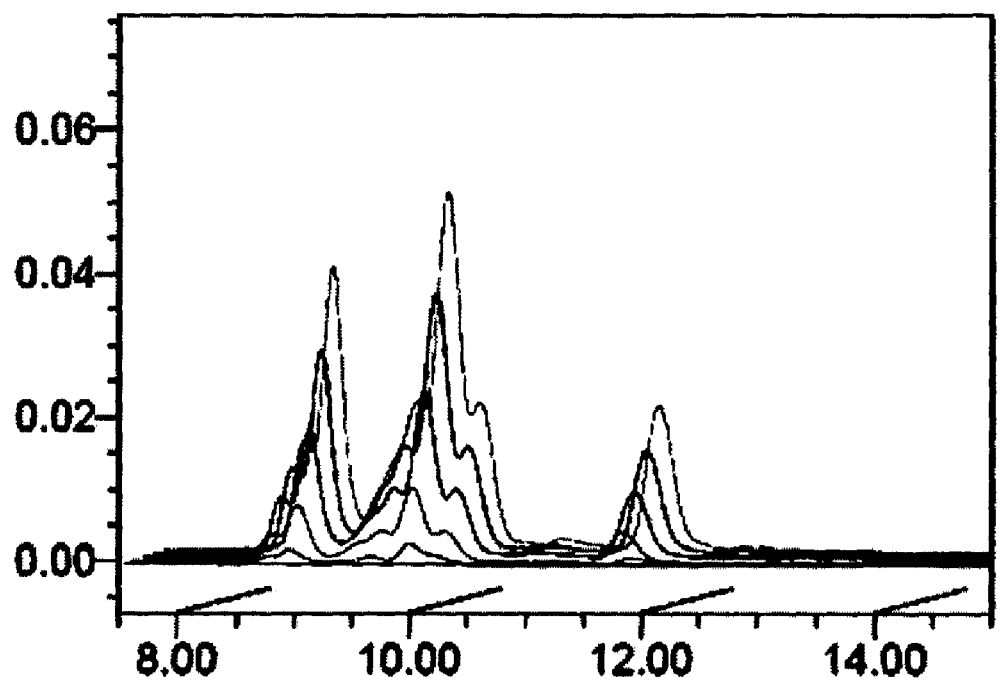
FIG. 3 is a calibration curve of the transfer factor.
Figure 4:
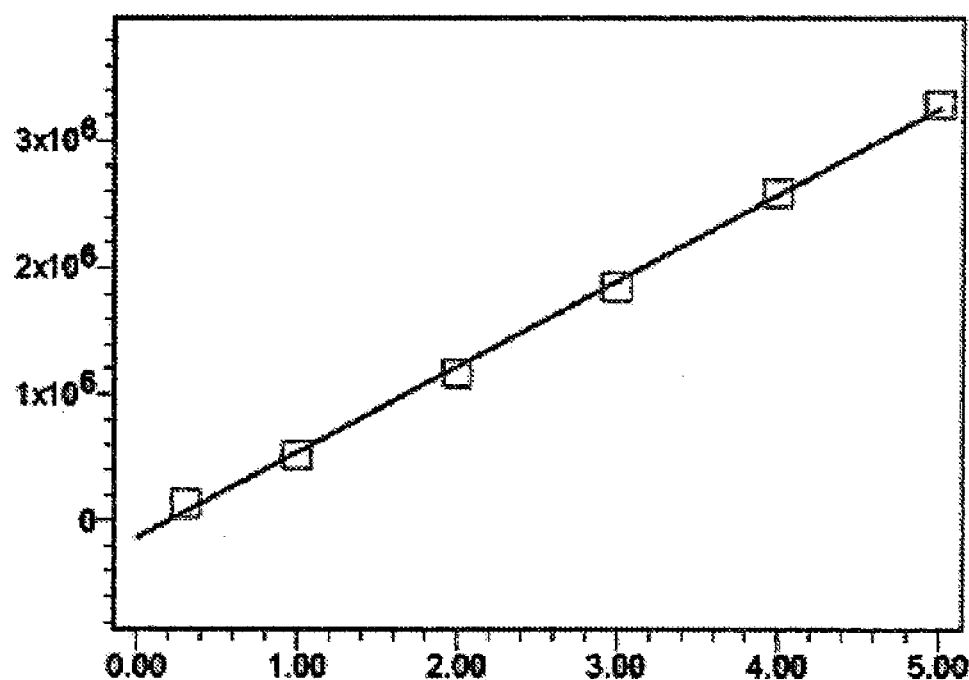
FIG. 4 is a calibration curve of the transfer factor.

Identification and Quantification Step by Ultra-resolution, Molecular-exclusion Liquid Chromatography This step was carried out under conditions for qualitative and quantitative analysis by SEC-UPLC in an Acquity UPLC system System Class H using the molecular-exclusion column Acquity BEH200 1.7 um 4.6×150 mm. Peptide separation was made with a 50 mM phosphate buffer solution with 50 mM sodium chloride at pH 7.0 and an isocratic flow rate of 0.2 ml/min, with a total elution time of 15 min. The above chromatographic conditions were used to obtain a calibration curve for the quantitative determinations. Chromatographic profiles were obtained from transfer factor Lot 11 B01, where 11 characteristic peaks can be observed, these results are shown in FIG. 1. These 11 peaks elute in a retention time ranging between 8.5 and 13.5 min. The molecular weight standards are shown in FIG. 2. Once obtained the characteristic peaks for the transfer factor, a calibration curve was made using a batch of transfer factor as internal standard, by injecting different volumes: 0.3, 1, 2, 3, 4 y 5 µL. Data were processed using the Empower software applications for the construction of the calibration curve, the results are shown in FIGS. 3 and 4.

This chromatographic method allow to perform a qualitative analysis to detect the 11 transfer facto characteristic peaks in a retention time ranging from 8.5 to 13.5 minutes. To know the molecular weight approximated range of the transfer factor peptide population, Bioarf molecular weight markers (1.35-670 kDa) and tryptophan (62 Daltons) were used, so we can infer that the transfer factor peptides have a molecular weight less than 17 kDa corresponding to the myoglobin of the Biorad standard. However, since the GPC application of the Empower software is missing, it is not possible to accurately determine the molecular weight of each peak, therefore, these are reported as lower than 17 kDa and with a retention time ranging from 8.5 to 13.5 min. On the other hand, a low range molecular weight marker is not available, reason why only tryptophan was used as a reference to an approximated molecular weight of 62 Daltons. With respect to the quantitative method, the calibration curve was obtained with a correlation coefficient r2 of 0.99, indicating a linear method fulfilling the acceptance criteria set as >0.98. In view of the above, the method can also be used for quantitative determinations.

EXAMPLE 5

In vitro Biological Validation Step

MG-63 cell line (ATCC CRL-1427) is human osteosarcoma cells. MG-63 cells were seeded in CORNING 12 well culture plates at a density of $1\times10^4$ cells per well in 500 □l MMSE culture medium (GIBCO cat. No. 30-2003) supplemented with 10% FBS (GIBCO Cat No. 16000-044), the stimulated cells are treated with transfer factor at a concentration of 100 □g/ml, a proliferation control is placed, with non-stimulated cells. The cells are incubated over 24, 48 and 72 hours. The experiment was performed in triplicate in each condition.

Figure 6:
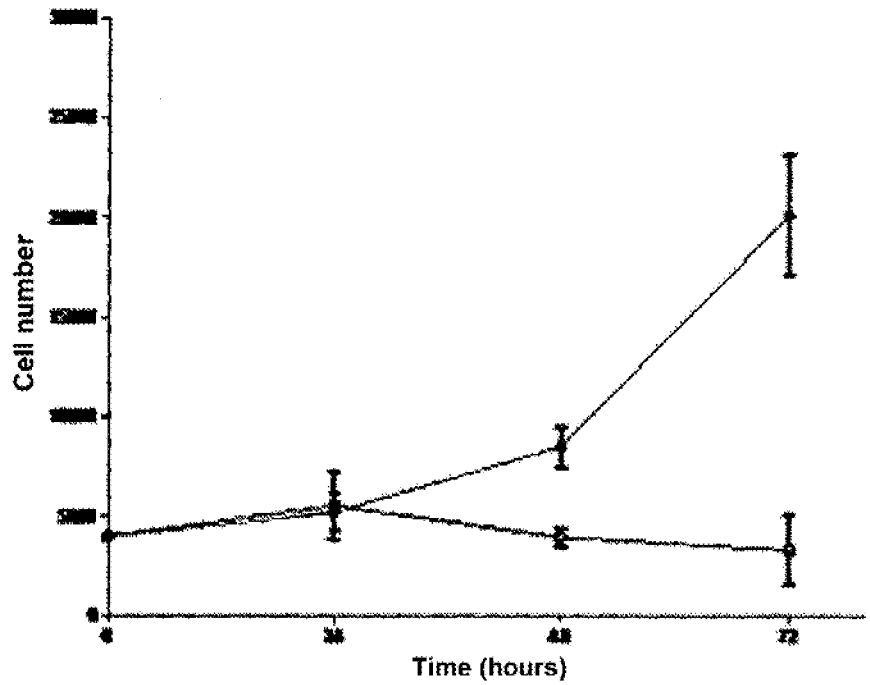
FIG. 6 is a graph corresponding to the effect of the transfer factor on the cell line A20 proliferation.

Proliferation Determination by Exclusion of Trypan Blue. After each incubation time, the number of cells and cellular viability are determined by the 0.4% trypan blue dye exclusion test (SIGMA Cat No. T8124). The cells are detached by trypsinization (triple GIBCO Cat No. 12563) and are centrifuged at 125×g for 5 min, then the counting is performed in a Neubauer chamber (FIG. 6).

The effect of the transfer factor on the cell line was determined using 3-(4,5-dimethylthiazol-2-yl)-2,5-diphenyltetrazolium bromide (MTT) Briefly, $1\times10^4$ cells/well were treated with 100 □g/ml. After incubating for 24, 48 and 72 hours, the cells were washed twice with phosphate saline solution (PBS) and TT (0.5 mg/ml PBS) was added to each well and incubated at 37° C. for 30 minutes. The formazan crystals that were formed were dissolved by adding dimethylsulphoxide (100 µL/well), and the absorbance was read at 570 nm using a microplate reader (Model 3550; BIO-RAD, Richmond, USA). The reduction in cell viability after the treatment with transfer factor is expressed in terms of control cells (non-treated cells). The percentages of cell survival were calculated as follows: % Of cell survival=(absorbance of treated cells/absorbance of cells with vehicle solvent)×100. The mean inhibitory concentration ($IC_{50}$) is calculated from dose-response curve obtained by plotting the percentage of cellular survival versus the concentration of transfer factor.

The same tests were also performed in AT20 cells, which are murine B cells from mice neoplasia of the BALB/cAnN strain. A20 cells are seeded in CORNING 96 well culture plates at a density of $4\times10^3$ cells per well in 200 □l RPMI culture medium (GIBCO) supplemented with 10% FBS (GIBCO), 0.05 mM 2-mercaptoethanol (SIGMA), the stimulated cells are treated with transfer factor at a concentration of 100 □l/ml, a proliferation control is placed with non-stimulated cells. The cells are incubated over 24, 48 and 72 hours. The experiment was performed in triplicate in each condition.

Figure 5:
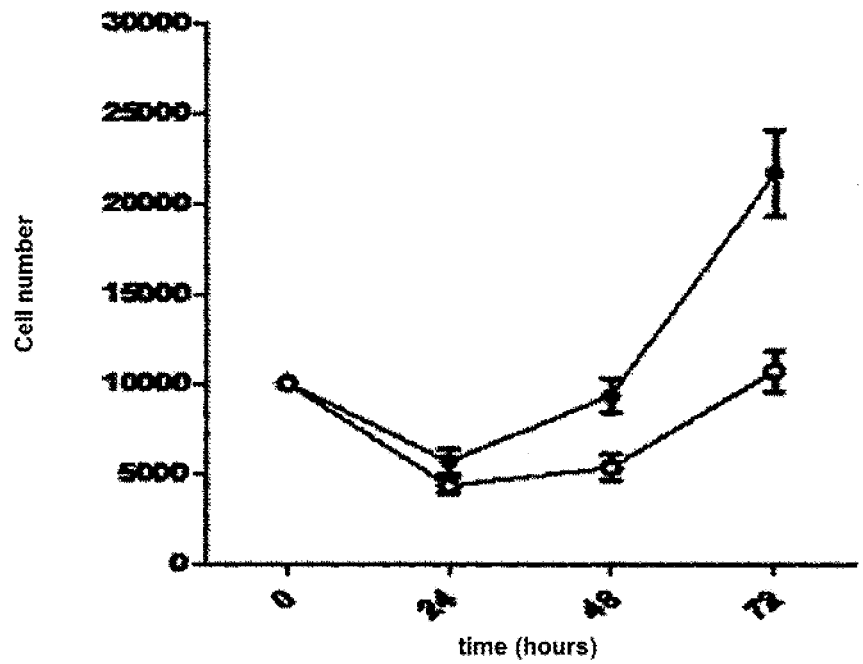
FIG. 5 is a graph corresponding to the effect of the transfer factor on the cell line MG-63 proliferation.

Proliferation Determination by Exclusion of Trypan Blue. After each incubation time the cell number and cellular viability are determined by the 0.4% trypan blue dye exclusion test (SIGMA Cat No. T8124). Cells are centrifuged at 125×g over 5 min, then the counting is performed in a Neubauer chamber (FIG. 5).

A20 cells are seeded in CORNING 96 well culture plates at a density of $4\times10^3$ cells per well in 200 □l MMSE culture medium (GIBCO Cat. No. 30-2003) supplemented with 10% FBS (GIBCO Cat No. 16000-044), the stimulated cells are treated with transfer factor at a concentration of 100 □g/ml, a proliferation control is placed, with non-stimulated cells. The cells are incubated over 24, 48 and 72 hours. The experiment was performed in triplicate in each condition.

For the MTT assay, 20 □l MTT solution is added (5 mg/ml in PBS) to each well, 3 h before each of the desired time points, and the cells are incubated at 37° C. for 3 h. After the incubation time, the culture medium is removed and 100 □l DMSO is added in each well. The plate is gently shaked on an orbital shaker for 10 minutes to completely dissolve the precipitation. The absorbance is read at 570 nm using an Epoch microplate reader (Biotek USA).

The invention claimed is:

1. A process for producing a transfer factor, comprising the following steps:
    a) subjecting a leukocyte concentrate to five freeze-thaw cycles, wherein, in each cycle, the concentrate is frozen at −20° C. for one week, and then completely thawed, to obtain a freeze-thaw product,
    b) subjecting the freeze-thaw product of step (a) to dialysis using a dialysis membrane with a 12 kDa cutoff, to obtain a dialyzed product:
    c) subjecting the dialyzed product of step (b) to serial tangential ultrafiltration, first with a 10 kDa cutoff and then with a 1 kDa cutoff, to obtain an ultrafiltrated product; wherein said ultrafiltrated product of step (c) is characterized by eleven peaks, said peaks eluting at approximate retention times of:

Peak No. Retention time (min)
1 8.7
2 8.85
3 9.4
4 9.6
5 10.0
6 10.2
7 10.6
8 10.9
9 11.1
10 11.8
11 12.15 when the ultrafiltrated product of step (c) is subjected to an Acquity UPLC system System Class H using the molecular-exclusion column Acquity BEH200 1.7 um 4.6×150 mm with a peptide separation with a 50 mM phosphate buffer solution with 50 mM sodium chloride at pH 7.0 and an isocratic flow rate of 0.2 ml/min, and wherein said ultrafiltrated product produced in step (c) is a transfer factor that has anti-proliferative activity.

2. The product obtained by the process of claim 1.

3. The method according to claim 1, wherein the anti-proliferative activity of the transfer factor is assayed by 3-(4,5-dimethylthiazol-2-yl)-2,5-diphenyltetrazolium bromide assay.

4. The method according to claim 1, wherein of the transfer factor inhibits proliferation of osteosarcoma cells.

5. The method according to claim 1, wherein of the transfer factor inhibits proliferation of AT20 cells.

* * * * *